(12) United States Patent
Riederer et al.

(10) Patent No.: US 9,700,229 B2
(45) Date of Patent: Jul. 11, 2017

(54) SYSTEM AND METHOD FOR IMBEDDED, HIGH-SPATIAL RESOLUTION, FLUOROSCOPIC TRACKING OF MULTI-STATION, CONTRAST-ENHANCED MAGNETIC RESONANCE ANGIOGRAPHY

(75) Inventors: Stephen J. Riederer, Rochester, MN (US); Casey P. Johnson, Iowa City, IA (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 13/435,547

(22) Filed: Mar. 30, 2012

(65) Prior Publication Data

US 2012/0253175 A1 Oct. 4, 2012

Related U.S. Application Data

(60) Provisional application No. 61/470,550, filed on Apr. 1, 2011.

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/004* (2013.01); *A61B 5/7285* (2013.01);
(Continued)

(58) Field of Classification Search
CPC ....... A61B 5/055; A61B 5/7285; A61B 5/004; G01R 33/5635; G01R 33/5619; G01R 33/5611; G01R 33/56383; G01R 33/4824
(Continued)

(56) References Cited

U.S. PATENT DOCUMENTS 5,417,213 A 5/1995 Prince
6,311,085 B1 10/2001 Meaney et al.
(Continued)

FOREIGN PATENT DOCUMENTS

WO WO2010/045018 * 4/2010
WO WO 2010/045018 A1 * 4/2010

OTHER PUBLICATIONS

Abche et al., "Partial k-space MRI reconstruction using a modified Homodyne approach". Signal Processing Algorithms, Architectures, Arrangements, and Applications Conference Proceedings (SPA), 2010. pp. 56-61.*

(Continued)

*Primary Examiner* — Long V Le
*Assistant Examiner* — Colin T Sakamoto
(74) *Attorney, Agent, or Firm* — Quarles & Brady LLP (57) ABSTRACT

A method of producing a series of vasculature images over an extended field of view (FOV) larger than an FOV of an MRI system includes acquiring initial time-resolved image data from the vasculature and, during the acquiring process, reconstructing, in substantially real-time, a series of three-dimensional (3D) tracking images of the initial portion of the vasculature illustrating a current position of a contrast bolus in the vasculature as the contrast bolus passes through the initial portion of the vasculature. Based on a current position of the contrast bolus, the subject is moved to a subsequent imaging station to acquire subsequent time-resolved image data and reconstruct subsequent 3D tracking images of subsequent portions of the vasculature. This process is repeated and then an image is assembled that extends over the extended FOV using the initial time-resolved image data and the subsequent time-resolved image data.

19 Claims, 6 Drawing Sheets

(51) Int. Cl.
*G01R 33/563* (2006.01)
*G01R 33/48* (2006.01)
*G01R 33/561* (2006.01)

(52) U.S. Cl.
CPC ...... *G01R 33/5635* (2013.01); *G01R 33/4824* (2013.01); *G01R 33/5611* (2013.01); *G01R 33/5619* (2013.01); *G01R 33/56383* (2013.01)

(58) Field of Classification Search
USPC .......................................................... 600/420
See application file for complete search history.

(56) References Cited

U.S. PATENT DOCUMENTS

| | | | |
|---|---|---|---|
| 6,487,435 B2 | 11/2002 | Mistretta et al. | |
| 6,841,998 B1 | 1/2005 | Griswold | |
| 7,003,343 B2 | 2/2006 | Watts et al. | |
| 8,433,392 B2 * | 4/2013 | Riederer | 600/420 |
| 2002/0177771 A1 * | 11/2002 | Guttman et al. | 600/410 |

OTHER PUBLICATIONS

Markl et al., "Phase Contrast MRI with High Temporal Resolution by View Sharing". Magnetic Resonance Imaging 2001.*

Earls, et al., Hepatic Arterial-Phase Dynamic Gadolinium-Enhanced MR Imaging: Optimization with a Test Examination and a Power Injector, Radiology, 1997, 202:268-273.

Griswold, et al., Generalized Autocalibrating Partially Parallel Acquisitions (GRAPPA), Magnetic Resonance in Medicine, 2002, 47:1202-1210.

Haider, et al., 3D High Temporal and Spatial Resolution Contrast-Enhanced MR Angiography of the Whole Brain, Magnetic Resonance in Medicine, 2008, 60(3):749-760.

Johnson, et al., Time-Resolved Bolus-Chase MR Angiography with Real-Time Triggering of Table Motion, Magnetic Resonance in Medicine, 2010, 64:629-637.

Kim, et al., Test Bolus Examination in the Carotid Artery at Dynamic Gadolinium-Enhanced MR Angiography, Radiology, 1998, 206:283-289.

Lee, et al., Dynamic k-Space Filling for Bolus Chase 3D MR Digital Subtraction Angiography, MRM, 1998, 40:99-104.

Leiner, et al., Three-Dimensional Contrast-Enhanced Moving-Bed Infusion-Tracking (MoBI-track) Peripheral MR Angiography with Flexible Choice of Imaging Parameters for Each Field of View, Journal of Magnetic Resonance Imaging, 2000, 11(4):368-377.

Meaney, et al., Stepping-Table Gadolinium-Enhanced Digital Subtraction MR Angiography of the Aorta and Lower Extremity Arteries: Preliminary Experience, Radiology, 1999, 211:59-67.

Noll, Homodyne Detection in Magnetic Resonance Imaging, IEEE Transactions on Medical Imaging, 1991, 10(2):154-163.

Pruessmann, et al., SENSE: Sensitivity Encoding for Fast MRI, Magnetic Resonance in Medicine, 1999, 42:952-962.

Riederer, et al., MR Fluoroscopy: Technical Feasibility, Magnetic Resonance in Medicine, 1988, 8(1):1-15.

Watts, et al., Anatomically Tailored k-Space Sampling for Bolus-Chase Three-Dimensional MR Digital Subtraction Angiography, Radiology, 2001, 218:899-904.

Weiger, et al., 2D Sense for Faster 3D MRI, Magnetic Resonance Materials in Physics, Biology and Medicine, 2002, 14:10-19.

Wilman, et al., Fluoroscopically Triggered Contrast-Enhanced Three-Dimensional MR Angiography with Elliptical Centric View Order: Application to the Renal Arteries, Radiology, 1997, 205:137-146.

Wilman, et al., Performance of an Elliptical Centric View Order for Signal Enhancement and Motion Artifact Suppression in Breath-hold Three-Dimensional Gradient Echo Imaging, MRM, 1997, 38:793-802.

\* cited by examiner

SYSTEM AND METHOD FOR IMBEDDED, HIGH-SPATIAL RESOLUTION, FLUOROSCOPIC TRACKING OF MULTI-STATION, CONTRAST-ENHANCED MAGNETIC RESONANCE ANGIOGRAPHY

CROSS-REFERENCE

This application is based on, claims the benefit of, and incorporates herein in its entirety by reference, U.S. Provisional Application Ser. No. 61/470,550, entitled "SYSTEM AND METHOD FOR IMBEDDED, HIGH-SPATIAL RESOLUTION, FLUOROSCOPIC TRACKING OF MULTI-STATION, CONTRAST-ENHANCED MAGNETIC RESONANCE ANGIOGRAPHY," and filed Apr. 1, 2011.

STATEMENT REGARDING FEDERALLY SPONSORED RESEARCH

This invention was made with government support under HL070620 awarded by the National Institutes of Health. The government has certain rights in this invention.

BACKGROUND OF THE INVENTION

The present invention relates generally to magnetic resonance imaging ("MRI") systems and methods and, more particularly, the invention relates to systems and methods for performing contrast-enhanced magnetic resonance angiography (CE-MRA) of a subject using high-spatial resolution, fluoroscopic images imbedded within the CE-MRA study as a trigger for coordinating the CE-MRA study with delivery of the contrast to the periphery.

Magnetic resonance imaging ("MRI") uses the nuclear magnetic resonance ("NMR") phenomenon to produce images. When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment $M_{xy}$. A signal is emitted by the excited nuclei or "spins," after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp," a "Fourier," a "rectilinear," or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

Magnetic resonance angiography (MRA) uses the magnetic resonance phenomenon to produce images of the human vasculature. To enhance the diagnostic capability of MRA a contrast agent such as gadolinium can be injected into the patient prior to the MRA scan. Typically a moderate amount (10-30 ml) of a gadolinium-based contrast agent is injected into an arm vein. The contrast material then mixes with the systemic blood in the heart and pulmonary vasculature and passes from the left heart into the arterial circulation. The presence of contrast material in the blood causes the net T1 relaxation time to be altered from its unenhanced value, for example, of about 1000 msec to values in the range, for example, of 50 to 100 msec. MR acquisition methods can exploit this change in T1, causing the enhanced blood within the vasculature to be significantly brighter compared to other structures within the imaging FOV.

There are a wide variety of technical challenges to performing CE-MRA to yield the desired information for a particular setting. As described in U.S. Pat. No. 5,417,213 the trick with this CE-MRA method is to acquire the central k-space views at the moment the bolus of contrast agent is flowing through the vasculature of interest. Collection of the central lines of k-space during peak arterial enhancement is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. In many anatomic regions, such as the carotid or renal arteries, the separation between arterial and venous enhancement can be as short as 6 seconds. However, this timing constraint is in opposition with the need to obtain a high spatial resolution image, for example, a three-dimensional (3D) image with adequate spatial resolution. To do so, it is necessary to have a sufficiently long acquisition time, generally in the range of ten seconds or longer, in order to collect enough information to yield the desired spatial resolution The short separation time between arterial and venous enhancement dictates the use of acquisition sequences of either low spatial resolution or very short repetition times (TR). Short TR acquisition sequences severely limit the signal-to-noise ratio (SNR) of the acquired images relative to those exams in which longer TRs are possible. The rapid acquisitions required by first-pass CE-MRA methods thus impose an upper limit on either spatial or temporal resolution.

As a result, depending on the technique used and the trade-offs that may be tolerated in a given clinical setting, it may be possible to utilize one of a variety of different strategies that have been developed to shorten the scan time. For example, one such strategy is referred to generally as "parallel MRI" ("pMRI"). Parallel MRI techniques use spatial information from arrays of radio frequency ("RF") receiver coils to substitute for the spatial encoding that would otherwise have to be obtained in a sequential fashion using RF pulses and magnetic field gradients, such as phase and frequency encoding gradients. Each of the spatially independent receiver coils of the array carries certain spatial information and has a different spatial sensitivity profile. This information is utilized in order to achieve a complete spatial encoding of the received MR signals, for example, by combining the simultaneously acquired data received from each of the separate coils.

Parallel MRI techniques allow an undersampling of k-space by reducing the number of acquired phase-encoded k-space sampling lines, while keeping the maximal extent covered in k-space fixed. The combination of the separate MR signals produced by the separate receiver coils enables a reduction of the acquisition time required for an image, in comparison to a conventional k-space data acquisition, by a factor generally bounded by the number of the receiver coils. Thus, the use of multiple receiver coils acts to multiply imaging speed, without increasing gradient switching rates or RF power.

Two categories of such parallel imaging techniques that have been developed and applied to in vivo imaging are so-called "image space methods" and "k-space methods." An exemplary image space method is known in the art as sensitivity encoding ("SENSE"), while an exemplary k-space method is known in the art as simultaneous acquisition of spatial harmonics ("SMASH"). With SENSE, the undersampled k-space data is first Fourier transformed to produce an aliased image from each coil, and then the aliased image signals are unfolded by a linear transformation of the superimposed pixel values. With SMASH, the omitted k-space lines are synthesized or reconstructed prior to Fourier transformation, by constructing a weighted combination of neighboring k-space lines acquired by the different receiver coils. SMASH requires that the spatial sensitivity of the coils be determined, and one way to do so is by "autocalibration" that entails the use of variable density k-space sampling. A more recent advance to SMASH techniques using autocalibration is a technique known as generalized autocalibrating partially parallel acquisitions ("GRAPPA"), as described, for example, in U.S. Pat. No. 6,841,998. With GRAPPA, k-space lines near the center of k-space are sampled at the Nyquist frequency, in comparison to the undersampling employed in the peripheral regions of k-space. These center k-space lines are referred to as the so-called autocalibration signal ("ACS") lines, which are used to determine the weighting factors that are utilized to synthesize, or reconstruct, the missing k-space lines.

When applied to CE-MRA acquisitions, short repetition time (TR) gradient echo sequences allow rapid collection of MRI data, and this can be accelerated with undersampling techniques such as SENSE and GRAPPA. Synchronizing the acquisition to the contrast arrival can be done using a test bolus or fluoroscopic triggering, such as described by Wilman A H, Riederer S J, King B F, Debbins J P, Rossman P J, Ehman R L. Fluoroscopically-triggered contrast-enhanced three-dimensional MR angiography with elliptical centric view order: application to the renal arteries. Radiology 1997; 205:137-146. An extension of the acquisition duration well into the venous phase, but with negligible venous signal, can be done using various centric phase encoding view orders, such as described by Wilman A H, Riederer S J. Performance of an elliptical centric view order for signal enhancement and motion artifact suppression in breathhold three dimensional gradient echo imaging. Magn Reson Med 1997; 38:793-802.

Imaging of the peripheral vasculature, defined roughly as those vessels contained within the region extending from the pelvis to the feet, poses additional technical challenges. First, the volume to be imaged is longer than the active region of the magnet system of the MRI system and, thus, the field of view (FOV) available to the clinician. To address this initial challenge, CE-MRA of the peripheral vasculature is generally done by breaking the extended superior-inferior (S/I) region into a series of three to five individual "stations," each of which can be imaged individually within the FOV of the MRI system. That is, MRA data is acquired from a desired, large field of view that extends beyond the FOV of the MRI system by moving the patient table to a plurality of different locations during the scan and acquiring an image at each station. The movement of the table should ideally be timed to follow the contrast bolus through the vasculature so that peak arterial contrast is imaged at each station. One method for matching image acquisition to peak arterial contrast, but limited to the first station, is fluoroscopic triggering. When contrast arrival is observed fluoroscopically within the first station, the radiologist or technologist can trigger the 10-25 sec long 3D acquisition of that first station. However, at the time of triggering the real-time presentation of contrast advance ceases, and the observer has no knowledge about the subsequent speed of advance of the contrast bolus to subsequent stations. Because this speed of advance is a highly patient-specific parameter, this approach is prone to error. The operator is in effect "flying blindly."

A second issue is that it is desirable to acquire data for an adequately long time at a given station to insure adequate image quality and sufficient spatial resolution but still an adequately short time to allow the scanner to advance to the next station prior to any venous enhancement there. These are competing demands. Sometimes this is addressed by applying an inflatable compression cuff around the patient's thighs to inhibit or delay blood passage from the arterial to the venous beds. However, use of venous compression cuffs adds extra time to the CE-MRA exam, and arguably images a non-normal physiological situation.

A third issue, as alluded to above, is that the transit time of the contrast bolus along the peripheral vasculature is highly variable from patient to patient. An attempted solution to this problem is to first administer a small, 2 ml test bolus and observe the arrival time at one or more locations along the peripheral vasculature and use this information to guide the time spent at each station. Various means have been developed to provide accurate timing including: use of a small test injection of contrast as described by J. K. Kim, R. I. Farb, and G. A. Wright, Test Bolus Examination in the Carotid Artery at Dynamic Gadolinium-enhanced MR Angiography, Radiology, 1998, 206:283-289. However, use of a test bolus also adds to the overall exam time and provides undesirable background signal to the subsequent high contrast dose exam.

Despite the advent of these and other techniques for addressing the competing clinical challenges of CE-MRA acquisitions and generally improving CE-MRA, none of the above solutions is completely effective in controlling or balancing the competing clinical challenges of CE-MRA acquisitions, particularly when the clinical need dictates a CE-MRA study of the periphery of a subject.

It would therefore be desirable to provide a system and method for performing angiographic studies of the periphery of a subject that provides high spatial resolution imaging of the arterial vasculature with sufficient venous suppression, but without the need of extraneous processes that extend the overall procedure, such as the use of a preliminary test bolus or compression cuffs. Furthermore, such systems and methods should be patient-specific to yield desirable, patient-specific clinical information.

SUMMARY OF THE INVENTION

The present invention overcomes the aforementioned drawbacks by providing a system and method for high-resolution, fluoroscopic tracking of table motion in a multi-station, contrast-enhanced MR angiography study of the peripheral vasculature. The method combines high-speed MR imaging with interactive control of the patient table and allows the table position to track the contrast material in the blood in real time as it advances along the vascular system. The fluoroscopic images themselves have the spatial resolution and volume coverage to allow diagnostic interpretation. The method accounts for the markedly conflicting demands for high spatial resolution and high temporal resolution by synergistically incorporating various means for acceleration.

In accordance with one aspect of the invention, a method of producing a series of contrast-enhanced, time-resolved images of a vasculature of a subject over an extended field of view using a magnetic resonance imaging (MRI) system having a field of view that is less than the extended field of view is disclosed. The method includes step a), positioning the subject at an initial imaging station to image an initial portion of the vasculature of the subject with the MRI system, and step b), acquiring initial time-resolved image data from the vasculature of the subject using the MRI system. The method also includes step c), during step b) reconstructing, in substantially real-time, a series of three-dimensional (3D) tracking images of the initial portion of the vasculature of the subject illustrating a current position of a contrast bolus provided to the subject as the contrast bolus passes through the initial portion of the vasculature. The method further includes step d), based on a current position of the contrast bolus, moving the subject to a subsequent imaging station to image a subsequent portion of the vasculature of the subject with the MRI system, and step e) acquiring subsequent time-resolved image data from the vasculature of the subject using the MRI system. The method also includes step f), during step e) reconstructing, in substantially real-time, a series of 3D tracking images of the subsequent portion of the vasculature of the subject illustrating a current position of the contrast bolus provided to the subject as the contrast bolus passes through the subsequent portion of the vasculature, step g), repeating steps d) through f) until image data has been acquired using the field of view of the MRI system from across the extended field of view, and step h), assembling an image of the vasculature of the subject over the extended field of view using the initial time-resolved image data and the subsequent time-resolved image data.

In accordance with another aspect of the invention, a magnetic resonance imaging (MRI) system having a field of view and configured to produce a series of contrast-enhanced, time-resolved images of a vasculature of a subject over an extended field of view that is greater than the field of view of the MRI system. The MRI system includes a magnet system configured to generate a polarizing magnetic field about at least a portion of a subject arranged in the MRI system, a plurality of gradient coils configured to apply a gradient field to the polarizing magnetic field, and a radio frequency (RF) system configured to apply an excitation field to the subject and acquire MR image data therefrom. The system also includes a computer system programmed to at least carry out the steps of positioning the subject at an initial imaging station to image an initial portion of the vasculature of the subject within the field of view of the MRI system and acquiring initial time-resolved image data from the vasculature of the subject using the MRI system. The computer is further programmed, such that, during acquisition of the acquiring initial time-resolved image data, the computer reconstructs, in substantially real-time, a series of three-dimensional (3D) tracking images of the initial portion of the vasculature of the subject illustrating a current position of a contrast bolus provided to the subject as the contrast bolus passes through the initial portion of the vasculature. Based on a current position of the contrast bolus, the computer is programmed to move the subject to a subsequent imaging station to image a subsequent portion of the vasculature of the subject within the field of view of MRI system. The computer is also programmed to acquire subsequent time-resolved image data from the subsequent portion of the vasculature of the subject using the MRI system and, during such, reconstruct, in substantially real-time, a series of 3D tracking images of the subsequent portion of the vasculature of the subject illustrating a current position of the contrast bolus provided to the subject as the contrast bolus passes through the subsequent portion of the vasculature. The computer is further programmed to repeat steps moving, acquiring, and reconstructing of until image data has been acquired using the field of view of the MRI system from across the extended field of view. The computer is thus programmed to assemble an image of the vasculature of the subject over the extended field of view using the initial time-resolved image data and the subsequent time-resolved image data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
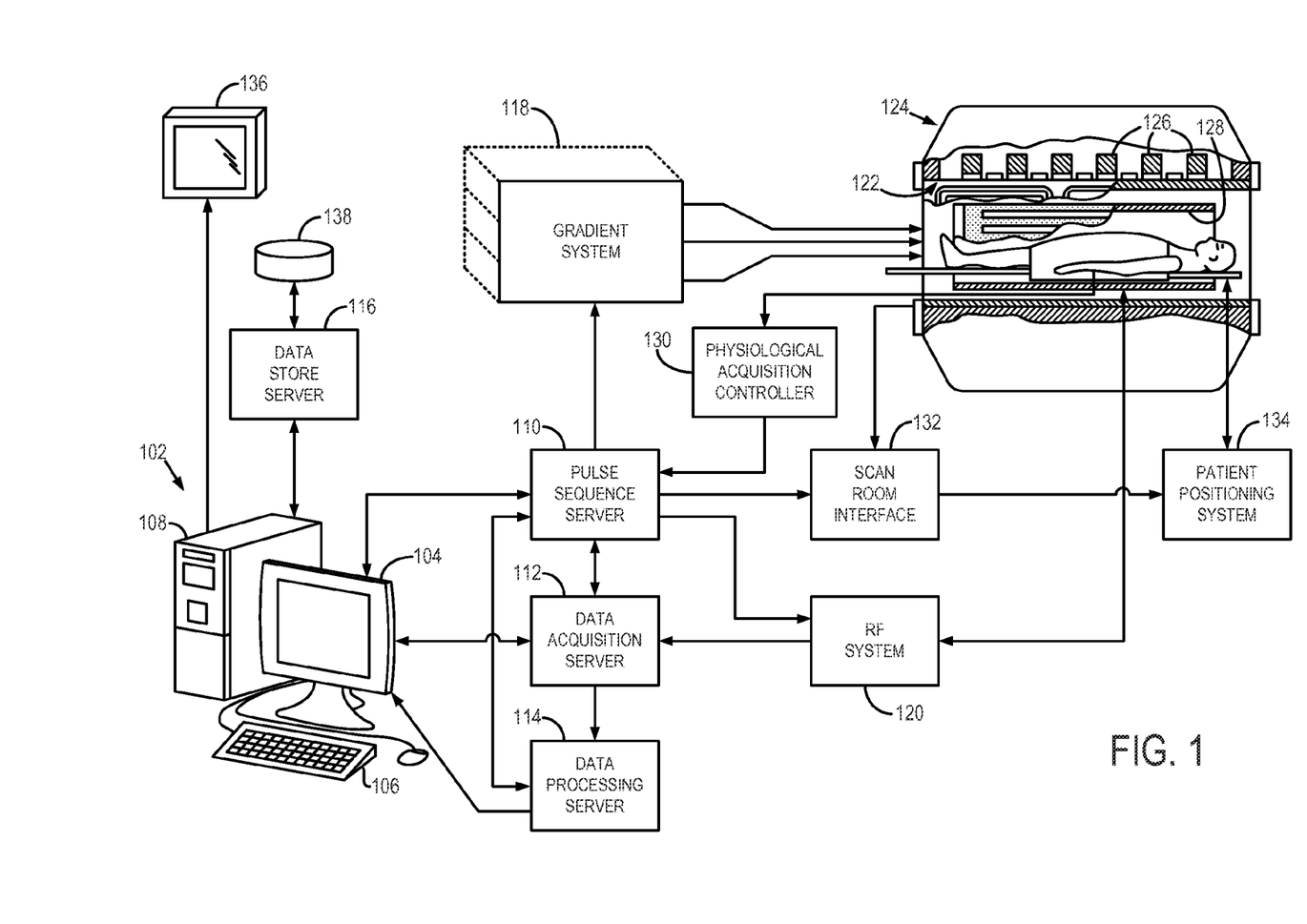
FIG. 1 is a block diagram of an exemplary magnetic resonance imaging ("MRI") system that employs the present invention.

Referring particularly to FIG. 1, an exemplary magnetic resonance imaging ("MRI") system 100 is shown. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad (1);$$

and the phase of the received MR signal may also be determined:

$$\phi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
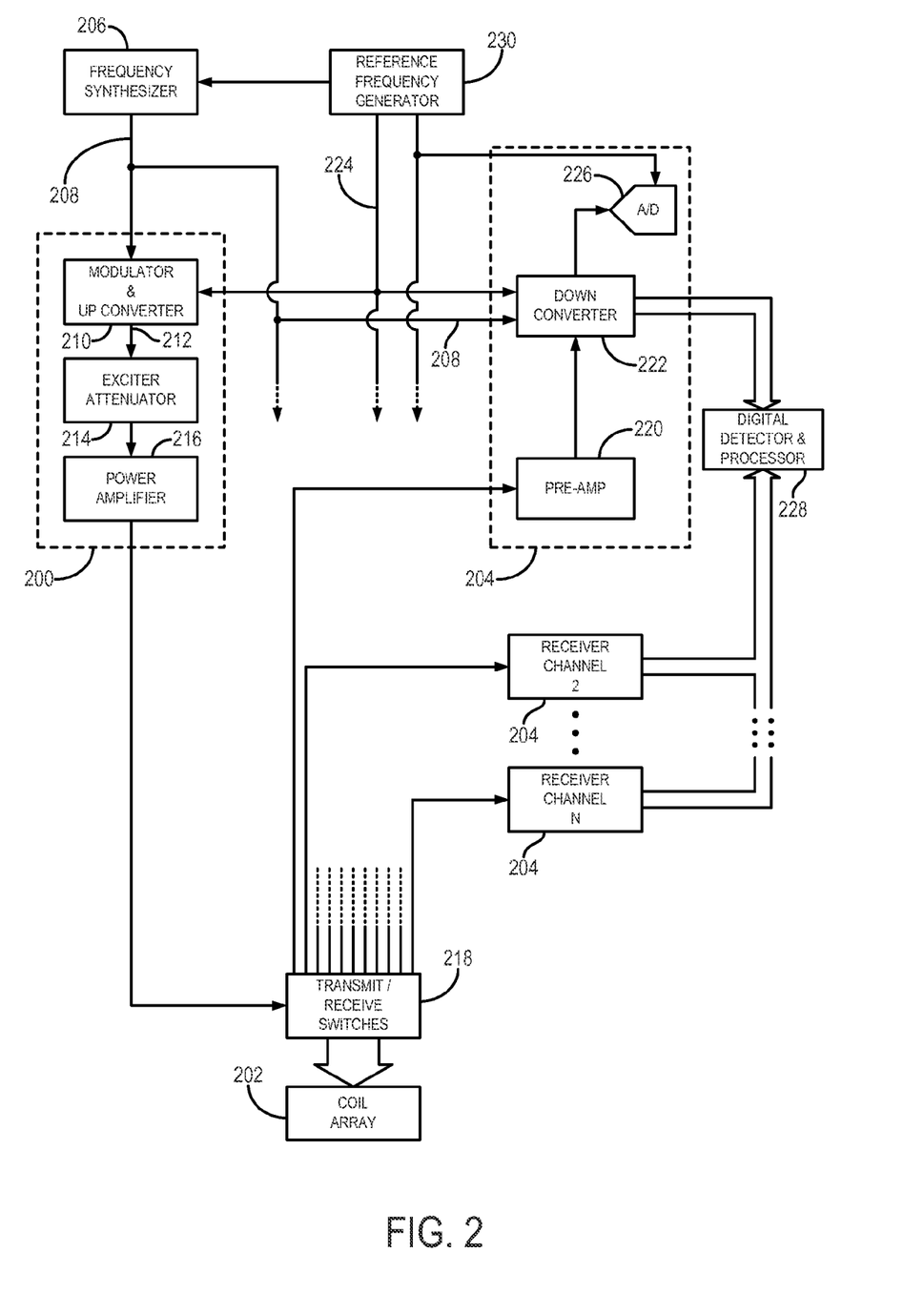
FIG. 2 is a block diagram of an exemplary radio frequency ("RF") system that forms a part of the MRI system of FIG. 1.

As shown in FIG. 1, the radio frequency ("RF") system 120 may be connected to the whole body RF coil 128, or as shown in FIG. 2, a transmitter section of the RF system 120 may connect to at least one transmit channel 200 of a coil array 202, and its receiver section may connect to at least one receiver channel 204 of the coil array 202. Often, the transmitter section is connected to the whole body RF coil 128 or a local transmit coil (not shown), and, in so-called "parallel receiver" coil arrays, each receiver section is connected to a separate receiver channel 204.

Referring particularly to FIG. 2, the RF system 120 includes a transmitter that produces a prescribed RF excitation field. The base, or carrier, frequency of this RF excitation field is produced under control of a frequency synthesizer 206 that receives a set of digital signals from the pulse sequence server 110. These digital signals indicate the frequency and phase of the RF carrier signal produced at an output 208. The RF carrier is applied to a modulator and up converter 210 where its amplitude is modulated in response to a signal, R(t), also received from the pulse sequence server 110. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 212 is attenuated by an exciter attenuator circuit 214 that receives a digital command from the pulse sequence server 110. The attenuated RF excitation pulses are applied to a power amplifier 216, which drives the RF coil array 202 through a transmit/receive ("T/R") switch 218.

Referring still to FIG. 2, the signal produced by the subject is picked up by the coil array 202 and applied to the inputs of a set of receiver channels 204. A pre-amplifier 220 in each receiver channel 204 amplifies the signal by an amount determined by a digital attenuation signal received from the pulse sequence server 110. The received signal is at or around the Larmor frequency, and this high frequency signal is down-converted in a two step process by a down converter 222, which first mixes the detected signal with the carrier signal on line 208 and then mixes the resulting difference signal with a reference signal on line 224. The down converted MR signal is applied to the input of an analog-to-digital ("N/D") converter 226 that samples and digitizes the analog signal and applies it to a digital detector and signal processor 228 that produces 16-bit in-phase (I) values and 16-bit quadrature (Q) values corresponding to the received signal. The resulting stream of digitized I and Q values of the received signal are output to the data acquisition server 112. The reference signal, as well as the sampling signal applied to the N/D converter 226, are produced by a reference frequency generator 230.

Using systems such as described above, the present invention allows high spatial resolution (3D) contrast "tracking" of the arterial vasculature with desirable venous suppression along an extended region, such as the peripheral vasculature. It does so without the need of a preliminary test bolus. It also allows this on a patient-specific basis.

As will be explained, the present invention distinguishes fluoroscopic "tracking" from "triggering." As explained above, fluoroscopic "triggering" is a prior-art technique in which a time series of images of a single slice is acquired and reconstructed in real time at a frame rate generally in the range of 0.5 to 2.0 Hz. Acquisition is generally done with a 2D technique. The slice is typically placed within or just upstream of a 3D volume targeted for a high spatial resolution 3D contrast-enhanced MRA study. The slice contains a portion of a large artery, such as the aorta, which is feeding the 3D volume. The purpose of fluoroscopic triggering is to allow the operator to observe in real time the arrival of the contrast-material-enhanced blood within the large artery, and once contrast has arrived allow him to rapidly (within 10-20 msec) switch from the fluoroscopic sequence to the high resolution, 20 sec or longer, 3D scan. Fluoroscopic triggering has very high reliability in guaranteeing that the 3D scan is initiated during the arterial phase of contrast material in the volume. However, because the fluoroscopic images are only of a single, thin (≤10 mm) slice, information about the 3D vasculature is not even generated. Thus, the fluoroscopic images themselves are simply used for timing and not used for diagnostic purposes in allowing analysis of the full 3D vasculature. Fluoroscopic triggering is, practically speaking, not used to trigger table motion to a new station because it is necessary to first collect the high spatial resolution 3D data for the current station. On the other hand, as will be described, the present invention enables fluoroscopic "tracking" by providing a time series of high-resolution (3D) images of a large volume, rather than a single slice, that enables the clinician to simultaneously: (i) generate high resolution images of the vasculature of the current station, and (ii) track the contrast agent advance in detail as it moves across the FOV and, thereby, determine when to move to a subsequent station based on the ongoing, detailed tracking images.

To better appreciate the technical demands of fluoroscopic tracking, it is informative to review spatial and temporal resolution parameters used in traditional "triggering" or "bolus chase" and time-resolved CE-MRA. The following table lists parameters for a number of bolus chase MRA studies using either a stepping table or continuously moving table approach as reported over the last decade.

| Author | Year | Method | Region | Spatial Resolution (mm$^3$) | Voxel Size (mm$^3$) | Image Update Time (sec) | Temporal Footprint (sec) |
|---|---|---|---|---|---|---|---|
| Meaney et al (7) | 1999 | Stepping Table | Pelvis/Thighs/Calves | 0.8 × 2.5 × 4.0 | 8.0 | 32 | 32 |
| Goyen et al (8) | 2002 | Stepping Table | Abd.-Calves | 1.5 × 1.7 × 3.0 | 7.6 | 12 | 12 |
| Maki et al (9) | 2002 | Stepping Table | Pelvis Thighs | 0.8 × 1.8 × 2.8 | 4.2 | 11 | 11 |
|  |  |  | Calves | 0.9 × 1.4 × 3.0 | 3.8 | 12 | 12 |
|  |  |  |  | 0.9 × 0.9 × 1.0 | 0.8 | 71 | 71 |
| Leiner et al (10) | 2004 | Stepping Table | Pelvis/Thighs Calves | 1.4 × 1.4 × 2.2 | 4.3 | 10-12 | 10-12 |
|  |  |  |  | 1.04 × 1.0 × | 1.8 | 60-75 | 60-75 |

-continued

| Author | Year | Method | Region | Spatial Resolution (mm³) | Voxel Size (mm³) | Image Update Time (sec) | Temporal Footprint (sec) |
|---|---|---|---|---|---|---|---|
| Madhuranthakam et al (11) | 2004 | CMT | Abd.-Thighs | 1.7 2.7 × 2.3 × 6.25 | 38.8 | 2.5 | 12.5 |
| Fain et al (12) | 2004 | CMT | Abd.-Calves | 1.6 × 1.6 × 1.6 | 4.1 | 6 | 6 |
| Fenchel et al (13) | 2005 | Stepping Table | Thighs | 1.0 × 1.6 × 1.5 | 2.4 | 13-17 | 13-17 |
| Madhuranthakam et al (14) | 2006 | CMT | Abd.-Thighs | 2.0 × 2.3 × 2.5 | 11.5 | 16 | 16 |
| | | | Calves | 2.0 × 1.2 × 1.3 | 3.1 | 50 | 50 |
| Nael et al (15) | 2007 | Stepping Table | Abd./Pelvis Thighs | 0.87 × 0.94 × 1.2 | 1.0 | 17 | 17 |
| | | | | 0.87 × 0.94 × 1.0 | 0.8 | 25 | 25 |
| Vogt et al (16) | 2007 | CMT | Abd.-Calves | 1.6 × 1.3 × 2.5 | 5.2 | 22 | 22 |
| Du et al (17) | 2008 | Stepping Table | Abdomen | 1.25 × 2.0 × 2.5 | 6.2 | >20 | >20 |
| Hadizadeh et al (18) | 2008 | Stepping Table | Upper Legs | 1.34 × 2.11 × 1.50 | 4.2 | 13.4 | 13.4 |
| Maki et al (19) | 2009 | Stepping Table | Abd./Pelvis | 1.2 × 2.1 × 2.6 | 6.6 | 8 | 8 |
| | | | Upper Legs | 1.2 × 2.1 × 2.6 | 6.6 | 10 | 10 |
| Nielsen et al (20) | 2010 | Stepping Table | Thighs | 1.38 × 1.38 × 3.40 | 6.5 | 20.8 | 20.8 |

Abd = abdomen,
CMT = continuously moving table.

Voxel sizes of images acquired at the abdomen, pelvis, thighs, and calves typically range from 1-8 mm3, and the time window to sample a given station, which is dependent on the voxel size, is usually no longer than about 20 sec. In most cases, only one image is formed at each proximal station. The exception is work done on time-resolved continuously moving table in Refs. (11) and (12), where rapid frame times were achieved at the expense of spatial resolution and image quality, making these methods more suitable for vessel localization and assessing the propagation speed of the contrast bolus than for diagnostic interpretation.

Additionally, the following table lists parameters for recent single-station time-resolved 3D CE-MRA studies of the calves.

| Author | Year | Method | Spatial Resolution (mm³) | Voxel Size (mm³) | Image Update Time (sec) | Temporal Footprint (sec) |
|---|---|---|---|---|---|---|
| Thornton et al (36) | 2006 | PR-hyperTRICKS | 0.8 × 2.5 × 4.0 | 3.7 | 4.3 | 90.3 |
| Wu et al (37) | 2009 | HYPR Stack-of-Stars | 0.8 × 0.8 × 1.6 | 1.0 | 5.6 | 89.6 |
| | | | 1.7 × 1.7 × 3.0 | 8.7 | 1.7 | 27.2 |
| Haider et al (4) | 2009 | CAPR | 1.0 × 1.0 × 1.0 | 1.0 | 5.0 | 17.7 |
| Lim et al (38) | 2010 | TWIST | 1.0 × 1.6 × 1.7 | 2.7 | 6.4 | 23.4 |

Compared to the bolus chase MRA parameters, these techniques have improved spatial resolution (typically 1-4 mm3 voxel size) and reduced frame times (typically 5 sec). However, the time window over which data must be acquired to ensure time frames have adequate diagnostic quality, as measured by the temporal footprint, is usually >20 sec. Long temporal footprints are allowed at the calves because this is the distal-most region studied, and there is no need for further table advance.

On the other hand, the fluoroscopic tracking technique of the present invention is designed to simultaneously satisfy a number of technical requirements at all but the most distal station of a bolus chase MRA protocol: (i) diagnostic spatial resolution along the three spatial dimensions competitive with that of state-of-the-art bolus chase MRA (e.g., 1.0 mm3); (ii) time-resolved imaging with frame times short enough to allow precise tracking of the advancing contrast bolus (e.g.,≤2.5 sec); (iii) formation of diagnostic angiograms at each station within approximately 20 sec as indicated above; and (iv) rapid (<1 sec) real-time reconstruction of time frames to allow precise triggering of table advance.

The 2.5 sec maximum frame time is based roughly on the 1.0 sec frame time identified for fluoroscopic triggering (30) as well as the potential need to trigger table advance within an imaging duration as short as 5 sec depending on the speed of bolus transit. Although frame times shorter than 2.5 sec might be desirable, there is a tradeoff with image quality. To meet these stringent demands using modern hardware capabilities, the fluoroscopic tracking sequence utilizes methods that provide high image acceleration, time-resolved sequences that are tailored to this specific application, and, as will be described, balances the tradeoffs to abate the consequences of undersampling.

Figure 3:
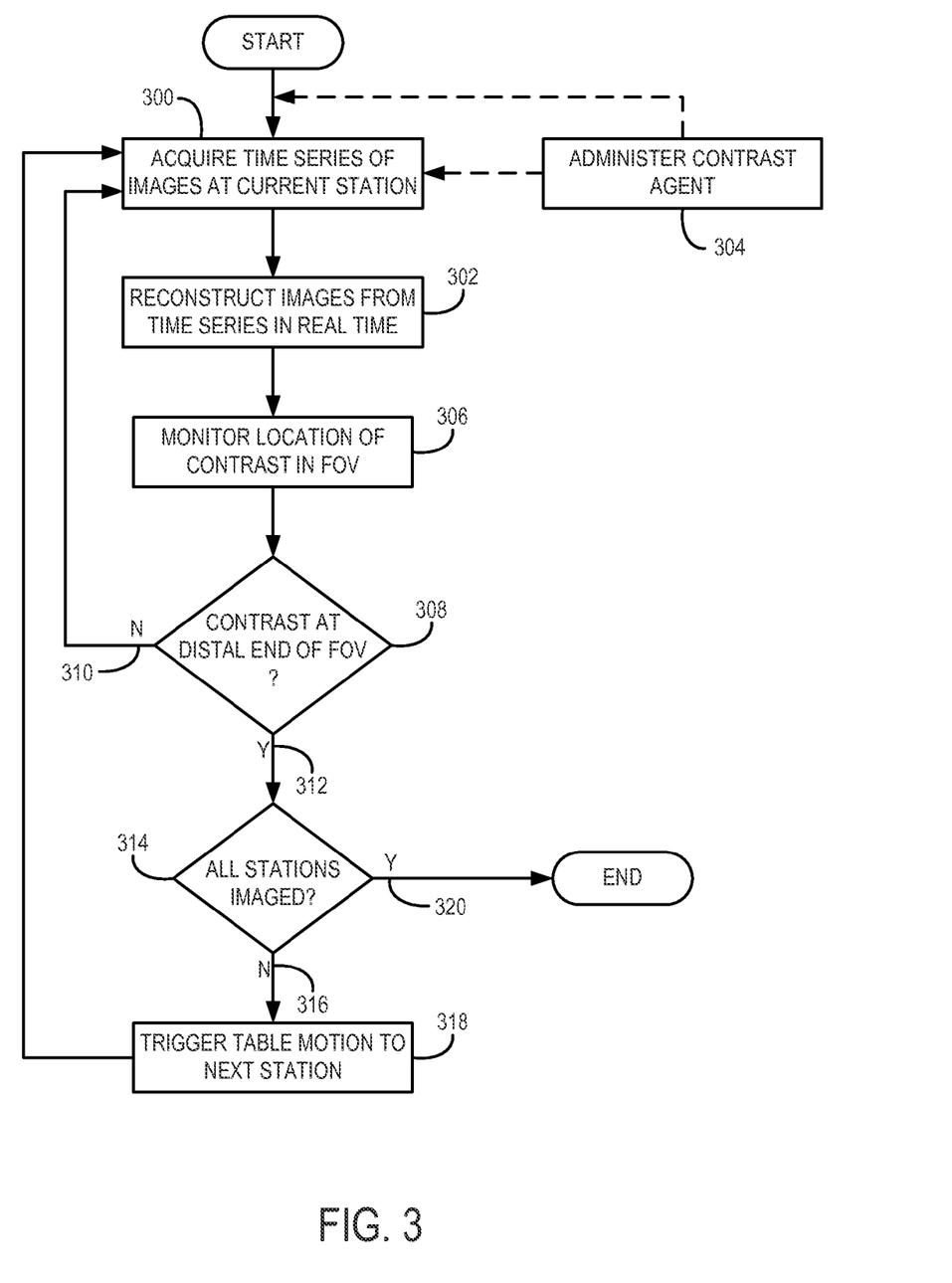
FIG. 3 is a flowchart setting forth the steps of a method for performing contrast enhanced magnetic resonance angiography (CE-MRA) process in accordance with the present invention.

Specifically, turning now to FIGS. 3 and 4, a process for high spatial-resolution tracking imaging of the arterial vasculature with desirable venous suppression along an extended region that is achieved using imbedded, high-resolution fluoroscopic images to coordinate multi-station movement will be described. For purposes of this example, three imaging stations in a multi-station MRA acquisition will be described. However, it is readily appreciated that the present invention is not limited to a particular number of stations.

The process begins at a first station, referred to hereafter as station 1, by acquiring a time series of images at station 1, as exemplified by process block 300. As illustrated in FIG. 4, a time series of images 400, such as those acquired as indicated at station 1, can be visualized as a series of image frames 402, each having a specific image frame time 404. As will be described in further detail, the frame time 404 is defined as the time between successive images presented to the observer. At process block 302, the acquired time series of images are reconstructed in real time, as acquired. This can be done using real-time reconstruction techniques, such as described in Wilman A H, Riederer S J, King B F, Debbins J P, Rossman P J, Ehman R L. Fluoroscopically-triggered contrast-enhanced three-dimensional MR angiography with elliptical centric view order: application to the renal arteries. Radiology 1997; 205:137-146, which is incorporated herein by reference. More recently, image reconstruction hardware upgrades have allowed high-speed reconstruction of 3D data sets, including those generated with the acceleration techniques of SENSE and Homodyne. For a data set approximately matching the resolution requirements described hereafter, the image reconstruction time is on the order of under 500 msec. Thus, the MR image acquisition results in a time series of images of the subject at station 1 presented continuously and generally contemporaneously with the image frame time 404 of the image frame 402.

As illustrated, at some time either before or after image acquisition begins at process block 300, a contrast agent is administered, typically intravenously, as illustrated by process block 304. Thus, the contrast-enhanced blood eventually arrives in the vasculature within the volume of the subject being imaged at station 1 and, accordingly, is reflected in the images being displayed in real time. Accordingly, whether performed by a clinician or automatically, the location of the contrast agent within the FOV of the MRI system, which is initially aligned at station 1, is monitored, as indicated at process block 306. As time and the image process progress, the contrast agent continues to advance through the subject and, within the images, can be seen to advance through the FOV from a proximal end of the images toward a distal end of the images. As indicated at decision block 308, the location of the contrast agent as it moves along the vasculature is monitored and, if not yet reaching the distal end of the FOV, as indicated at decision 310, the imaging acquisition at station 1 continues. However, once the contrast reaches the distal end of the FOV, as indicated at decision 312, a subsequent check is made at decision block 314 to determine if the current station being imaged is the last and, if not, as indicated at decision block 316, the patient table of the MRI system is moved to the next station, as indicated at process block 318.

Figure 4:
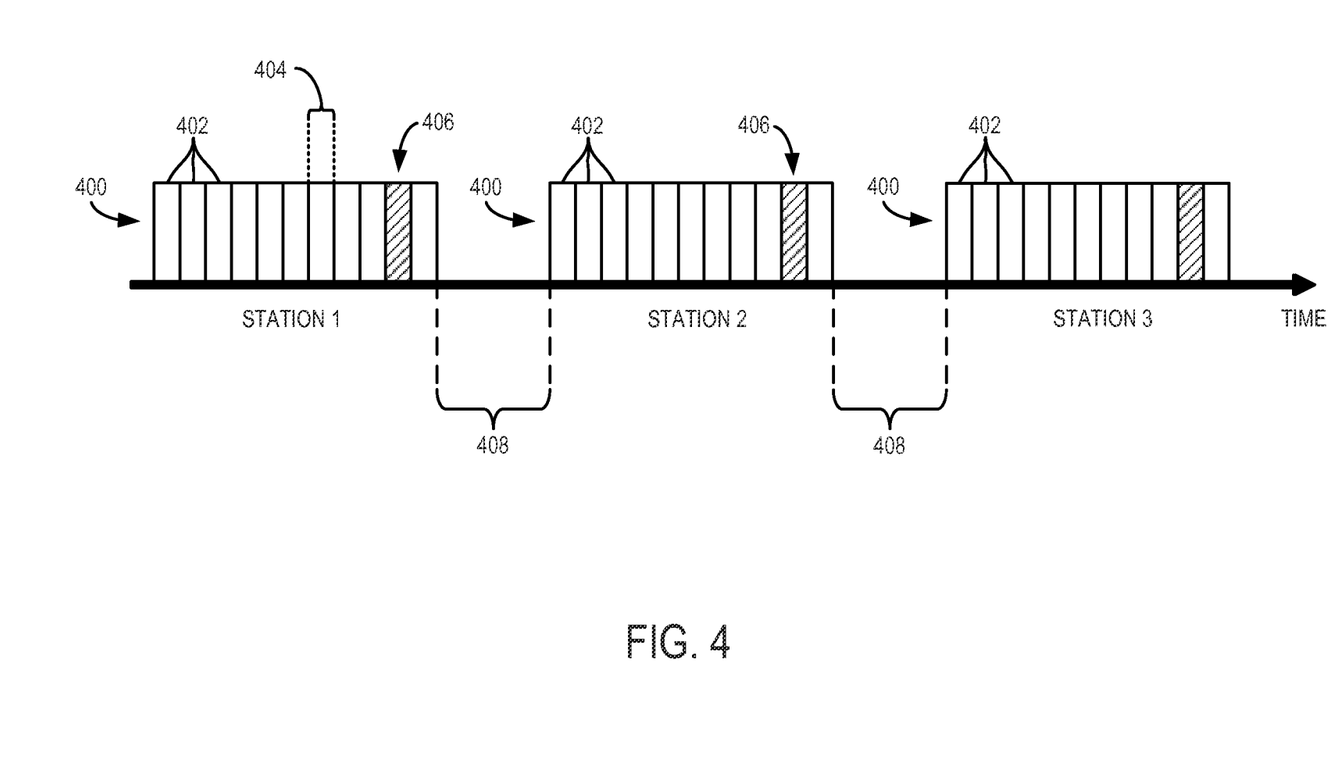
FIG. 4 is a timing diagram for an exemplary CE-MRA process in accordance with the present invention.

For example, as illustrated in FIG. 4, each image frame 402 will depict the contrast agent passing from a proximal end of the FOV toward a distal end. When an image frame 406 showing the contrast at the distal end or having advanced toward the distal end sufficiently is detected, either by a clinician or automated process, a command to move the table of the MRI system to the next station is issued. Given the duration of image frame times 402, this trigger of table motion generally occurs during the next image frame, at which time image acquisition and real-time reconstruction at station 1 is complete and the subject is moved to station 2 over a duration of table motion 408 over which imaging may be delayed. As illustrated in FIGS. 3 and 4, once the table is moved to the next station, the process is repeated until, at decision block 320, the imaging at the last station has been completed and the process ends.

As described above, the systems and methods of the present invention improves substantially upon traditional, low-resolution or non-imbedded fluoroscopic triggering of contrast-enhanced MR angiograms. However, as will be described, in clinical practice, it previously was unclear that it was possible to balance the competing constraints on imaging techniques and patient-specific imaging parameters to yield a clinically feasible protocol and clinically useful images. However, with the present invention, the above-described high-resolution, fluoroscopic tracking can be designed to provide accurate initiation of a single high spatial-resolution contrast-enhanced MR angiogram within a single volume.

In prior-art fluoroscopic triggering techniques, the fluoroscopic sequence used for monitoring generally interrogates only a single slice using a 2DFT acquisition technique. For a single slice, the acquisition time can be relatively short, such as 1.0 sec per image, to allow for precise timing. The spatial resolution is made coarse enough to allow this short frame time. Of course, these speed constraint yields fluoroscopic images low or degraded spatial resolution and limited, 2D slice, coverage. Thus, because the 2D slice fails to provide any of the desired 3D information about the full volume containing the vascular tree of interest, fluoroscopic images are not suitable for or designed to provide diagnostic information.

In contrast to such prior-art fluoroscopic triggering MRA techniques, with the fluoroscopic tracking technique described here, the acquired high-resolution (3D) fluoroscopic images are simultaneously suitable to provide real-time feedback and bolus tracking to accurately determine when to move to a subsequent station in a multi-station acquisition as well as provide high image quality, 3D volume coverage, and spatial resolution required for clinical use and diagnostic purposes.

However, in order to achieve the above-described clinical process, there are a number of substantial technical issues that must be addressed to provide a practical and useful clinical implementation. To best understand these challenges, the technical performance requirements for clinical usefulness should be considered. In order for the overall contrast-enhanced MR angiogram to have diagnostic value it is important that there be at least one 3D image generated at each station that has high spatial resolution. For clinical purposes, a useful target for the spatial resolution is approximately 1 mm in all three directions. Although this value may vary by specific clinical application and diagnostic need, it is useful to define a specific objective measure as a target. A second specification is the necessary overall field-of-view (FOV) to be covered. As a specific example, assuming, for example, that three stations are to be used, each might have a length of 35 cm superior/inferior (S/I), 32 cm left-right (L/R), and 12.8 cm anterior-posterior (A/P). In practice, this will of course vary from patient to patient.

Using these numerical values for FOV and spatial resolution for purposes of this example, it is possible to determine the degree of MRI data sampling necessary to form a 3D image at a given station. Assuming that a 3DFT acquisition is performed using a gradient echo sequence having repetition time TR with frequency encoding (X direction) S/I, phase encoding (Y) L/R, and slice encoding (Z) NP, the number of samples required in each direction is simply the ratio of the FOV with the spatial resolution. For example, in the present example, in the Y direction the number of samples is $N_Y$=32 cm/1 mm=320. Similarly $N_Z$=12.8 cm/1 mm=128. The total number of repetitions, $N_{TOT}$, necessary in a standard 3DFT acquisition is equal to the product $N_{TOT}$=$N_Y \times N_Z$. In this example, $N_{TOT}$ is thus 40,960. Assuming a TR value of 5 msec, then the acquisition time $T_{ACQ}$ necessary to generate the image is given by $T_{ACQ}$=$N_{TOT} \times TR$ or 204 sec in this example. Unfortunately, an acquisition time of 204 sec is impractically long to image a single station for multi-station peripheral CE-MRA. For example, with an acquisition time of 204 sec, it is doubtful that the contrast material would be retained at full concentration even within a single station, much less multiple stations to pass through the FOV. Thus, tracking using traditional fluoroscopic triggering protocols, but extended to provide the real-time, high-resolution images for triggering, would be rendered futile.

Another technical specification of the fluoroscopic tracking method is the frame time required for the real-time imaging process. As described above, the frame time is defined as the time between successive images presented to the observer as was shown schematically in FIG. 4. To closely match initiation of table motion from one station to the next with the transit of the contrast material, it is desirable to have the frame time be adequately small. Specifically, this duration should be no longer than several seconds. A frame time much longer than this may be so coarse that the contrast material could possibly pass along the entire extent of a station between frames. The subsequent detection of contrast passage would then be late. This, in turn, would cause the table motion to lag the contrast passage, yielding images in distal stations that would be initiated too late and subject to venous contamination. As a specific numerical example in this discussion we will use a frame time of 2 sec.

To summarize, a technically demanding set of constraints is presented to achieve the above-described fluoroscopic tracking method. Specifically, the acquisition of diagnostic-quality arteriograms with high spatial resolution (1.0 mm3) while also producing images with a short frame time (≤2.5 sec) in a limited acquisition time window (<20 sec). The above constraints and numerical examples serve to illustrate the fundamental incompatibility of the extensive acquisition time necessary for adequate spatial resolution (204 sec in this example) and the short frame time (2 sec) necessary for adequate precision of table advancement. This is a factor of 100× difference.

As identified above, one of the principal technical challenges of high-resolution fluoroscopic tracking is to provide image quality normally associated with an acquisition time of about 200 sec at a frame time of about 2 sec. To reconcile this discrepancy between constraints and achieve the above-described high-resolution fluoroscopic triggered multi-station MRA protocol, a variety of competing techniques are used despite a view that the techniques, in many clinical settings, are often viewed as being incompatible due to competing constraints. However, as will be explained, the present invention combines these techniques to overcome the above-described technical challenges and achieve the above-described high-resolution fluoroscopic triggered multi-station MRA protocol.

A first technique that is utilized includes view sharing. Specifically, the need for a short 2.5 sec frame time, but with allowance for a somewhat longer temporal footprint allows a view-shared sequence to be used for fluoroscopic tracking. When a time sequence of MR images is generated it is possible to share some of the acquired data from one image to the next, a technique referred to as "view sharing," such as described in Riederer S J, Tasciyan T, Farzaneh F, Lee J N, Wright R C, Herfkens R J. MR fluoroscopy: technical feasibility. Magn Reson Med 1988; 8:1-15, which is incorporated herein by reference. This allows the time between consecutive frames to be smaller than the acquisition time necessary to form a single image. This latter time is referred to as the "temporal footprint," as described in Haider C R, Hu H H, Campeau N G, Huston III J, Riederer S J. 3D high temporal and spatial resolution contrast-enhanced MR angiography of the whole brain. Magn Reson Med 2008; 60:749-760, which is incorporated herein by reference.

Many contemporary time-resolved imaging techniques used for 3D CE-MRA such as keyhole, TRICKS, CAPR, and TWIST make use of view sharing to provide frame times that are shorter than the intrinsic acquisition time of a given pulse sequence. Furthermore, the central region of k-space is typically sampled more frequently than peripheral k-space so as to provide a smoother portrayal of the dynamic phenomenon under study. Most 3D methods segment the kY-kZ phase encoding plane into a low spatial frequency center region, which encodes overall contrast information, and a high spatial frequency outer region, which provides additional detail. The relative sizes of each region, the temporal ordering of sampling of these regions, and the precise spatial frequencies included in each can have significant effects on spatiotemporal resolution.

The present invention recognizes that the temporal footprint may be three to eight times longer than the frame time, with the resultant time series of images still providing accurate depiction of a dynamic phenomenon. To take a specific example, allowance of a 7× longer temporal footprint than the target 2 sec frame time means that the resultant target acquisition time per image can be calculated using view sharing and the discovery that the temporal footprint may be three to eight times longer than the frame time as 7×2 sec or 14 sec.

Figure 5:
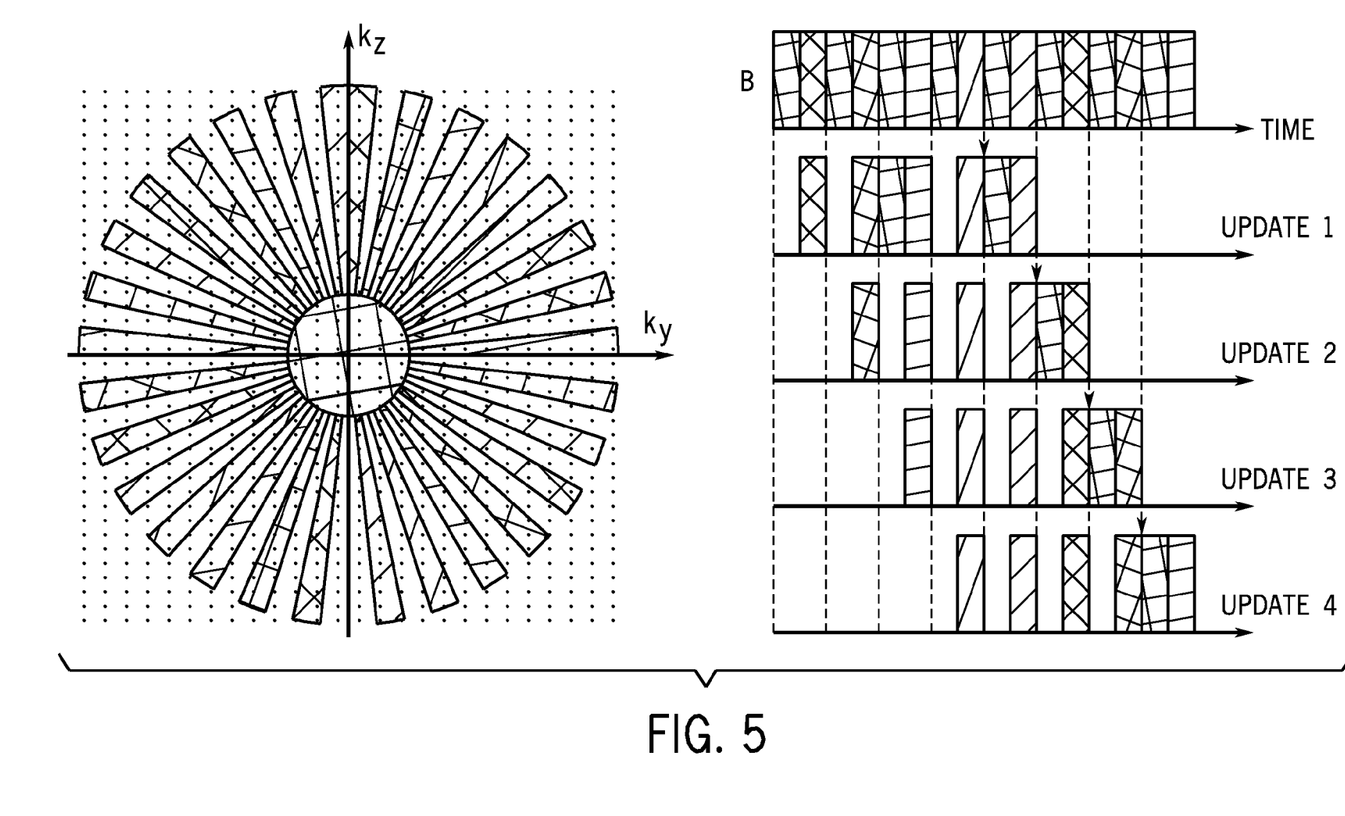
FIG. 5 is a diagram illustrating a k-space sampling and associated time frames in accordance with the use of a pulse sequence in accordance with the present invention.

Considering this, the k-space sampling pattern for CAPR is shown in FIG. 5 and consists of an lowpass center region and N (here 5) highpass vane sets. For every frame of a CAPR-generated time series, the central k-space region and one vane set are sampled and the data are used to update previous samplings of these regions. Data for the other N−1 vane sets are shared from the previous frame. This playout of views and the sorting used to form the first several images of a time series is illustrated.

Figure 6:
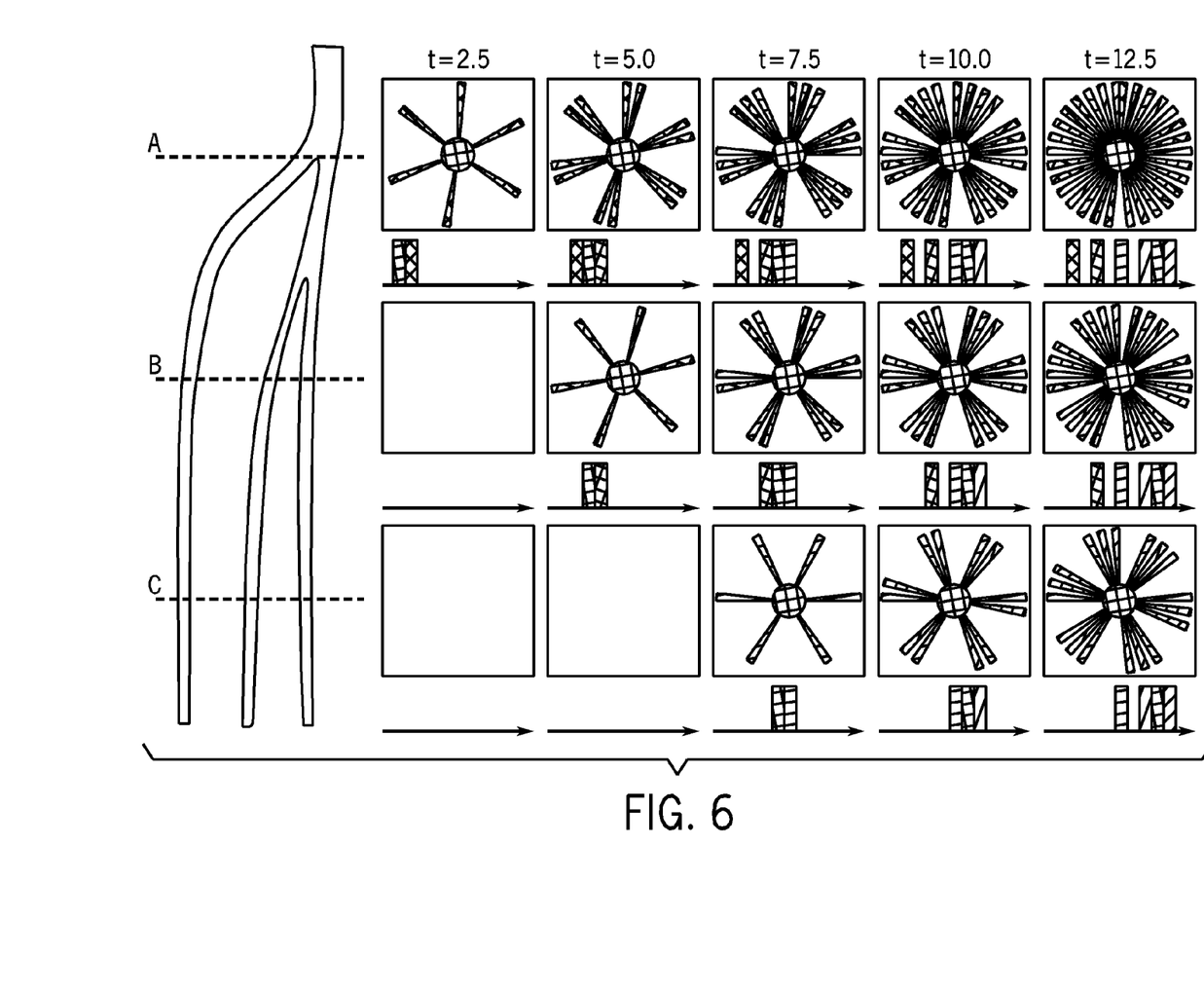
FIG. 6 is a diagram illustrating the use of a k-space sampling coordinated with a CE-MRA process in accordance with the present invention.

Next consider how k-space is sampled for the specific case of fluoroscopic tracking. Referring to FIG. 6, the vasculature of the calf of one leg is illustrated by accompanying k-space samplings. Consider how an image is built up as a function of contrast bolus arrival at the vessel locations (a-b-c) indicated by the dashed lines. Following arrival of the contrast bolus at a specific location, the bolus signal is initially encoded by the center and only one vane set. Progressive k-space sampling of subsequent vane sets adds additional detail to the sampled bolus. Therefore, contrast-enhanced vessels are only fully sampled if all vane sets are acquired with contrast material present. In FIG. 6, suppose the image update time is 2.5 sec and the contrast bolus arrives at the three locations, starting with the most superior (a), at times t=0, 2.5, and 5.0 sec. Also, suppose that imaging occurs for only 12.5 sec. After 12.5 sec all five vane sets will have been sampled at the first location (a), ideally yielding a sharp result. However, at the second and third locations (b and c) the k-space sampling is incomplete as seen by the incomplete vane patterns in the rightmost column of FIG. 6, and some degree of vessel blur or other artifact can be expected.

A second technique that is utilized includes SENSE acceleration. As briefly described above, SENSE is a method in which the redundancy of information collected by the use of multiple independent receiver coil elements can be used to reduce the number of repetitions necessary to form an image of given spatial resolution. The degree of time reduction is referred to as the acceleration, R. SENSE acceleration can be performed in one or two directions, with the latter possible in 3DFT acquisitions, such as used herein. With proper and careful design, a SENSE acceleration R=8 may be achieved within the context of the present invention without sacrificing image quality.

A third technique that is utilized is homodyne (HD) reconstruction. As is well known, because MR images are formed of actual objects, the MRI data in k-space have mathematical properties of symmetry. This means that data at a specific k-space position can be estimated from the measured data at a different, companion k-space position, obviating actual measurement at the first position. This process, called homodyne (HD) reconstruction, such as described in Noll D C, Nishimura D G, Macovski A. Homodyne detection in magnetic resonance imaging. IEEE Trans Med Img 1991; 10:154-163, which is incorporated herein by reference, theoretically allows a two-fold reduction in the amount of data that must be acquired. However, in the context of the present invention, it is noted that the use of homodyne reconstruction allows an acceleration ($R_{HD}$) of about 1.8.

The above-described three techniques can be used for enhancement of frame rate or reduction of acquisition time. However, they are independent of each other. In the context of the present invention, it was recognized that these three techniques can be applied synergistically by balancing competing constraints and properly selecting imaging parameters. View sharing allows the target acquisition time per image to be increased from 2 to 14 sec. This means that the target reduction in acquisition time for the fluoroscopic tracking images is 200 sec/14 sec or about 14.2. The net reduction in acquisition time, or net acceleration $R_{NET}$, which the present invention allows and is clinically practical by combining the methods of SENSE and homodyne is $R_{NET}=R \times R_{HD}$, which by way of the above exemplary constraints, is 8×1.8=14.4. As such, the present combination of techniques can be used to substantially match the target net acceleration of 14.2 and, thereby, achieve the FOV coverage, spatial resolution, and frame time desired for high-resolution fluoroscopic tracking during multi-station MRA.

Again, the above numerical values are used for illustration purposes and can and will vary by clinical and diagnostic constraints. Nevertheless, the present invention can be readily adapted to accommodate modified values of the specified parameters of spatial resolution, FOV, and frame time through modification of the techniques described above as well as other methods for acceleration, reduction of acquisition time, or enhancement of frame rate.

The following parameters are now defined: (i) image update time, defined as the time to sample a time frame; (ii) temporal footprint, defined as the temporal extent of information used to reconstruct a time frame (33); (iii) relative center diameter (C), defined as the dimensionless ratio of the diameter of the CAPR center region to the FOV of the phase encoding plane and assumed to be the same for both the kY and kZ directions (C=0 if there is no center and C=1 if there is no highpass region); and (iv) view share factor (N), defined as the number of CAPR highpass vane sets. The reference CAPR sequence for imaging the calves (4) uses four vane sets (N4) and a moderate relative center diameter of 0.31. Standard acquisition parameters in the phase encoding plane are: FOV=32.0 (L/R)×13.2 (NP) cm2; sampling matrix=320×132 (yielding 1.0 mm 2 spatial resolution); and 2D SENSE acceleration=4 (L/R)×2 (NP). Assuming TR=5.9 sec, the image update time and temporal footprint of this CAPR sequence can be calculated to be 5.0 sec and 17.7 sec, respectively. This sequence is identified by the circled "N4" of FIG. 3, a plot of temporal footprint vs. image update time for various CAPR implementations. Although this meets the spatial resolution and temporal footprint targets, the 5.0 sec update time is longer than the targeted 2.5 sec.

Assuming the FOV, nominal spatial resolution, and 2D SENSE acceleration of the reference protocol are fixed, the image update time must be reduced by either: (i) decreasing the relative center diameter (C); or (ii) increasing the view share factor (N). Using the reference acquisition parameters, the image update time and temporal footprint can be calculated for various values of C and N. To achieve an image update time no greater than 2.5 sec (dashed line), the view share factor must be greater than N4. One option is to use N5 CAPR with a small relative center diameter (C≤0.08). Alternatively, the view share factor can be increased to allow a more varied degree of relative center diameters; for example, N8 CAPR with C≤0.21. Sequences with a short temporal footprint, such as those with a small relative center diameter and view share factor, will produce the highest quality angiograms for fluoroscopic tracking.

The present invention demonstrates an improved time-resolved sampling technique, in combination with R=8 2D SENSE acceleration and asymmetrical undersampling, that meets the technical demands for the above-defined fluoroscopic tracking: (i) high spatial resolution (≤1.0 mm3); (ii) rapid image update time (2.5 sec); (iii) short temporal footprint (<12.5 sec); and (iv) real-time reconstruction of time frames with low latency. This combination of spatiotemporal parameters exceeds what has been shown in either the bolus chase or fluoroscopic tracking MRA or 3D time-resolved calf contrast-enhanced MRA literature, as outlined in the above tables.

There are two design considerations for a fluoroscopic tracking sequences. First, minimizing the temporal footprint of the fluoroscopic tracking sequence is important to allow more rapid sampling of the high spatial frequencies of k-space and thus the formation of sharp arteriograms at proximal stations. This can be accomplished by either reducing the imaging FOV or nominal spatial resolution or increasing the parallel imaging acceleration. However, if these parameters are fixed, the temporal footprint can be reduced by decreasing the view share factor. The consequential increase in image update time can then be offset by decreasing the relative center diameter, though at the expense of reduced signal in early time frames. Second, sampling effects on vessel signal and spatial resolution are dependent on the diameter of the vessel lumen in the phase encoding plane (measured in pixels). The proposed sampling strategy is substantially effective when imaging small vessels (FWHM<6 pixels). This is desirable, since peripheral artery disease is typically manifested by narrowing of the vessel lumen. Additionally, any reduction in spatial resolution, as may be acceptable when imaging large vessels of the abdomen, pelvis, or thighs, will favor the described technique.

The fluoroscopic tracking sequence described above can use the N5 CAPR sequence and can be flexibly altered depending on the specific imaging parameters used. For example, if 2D SENSE acceleration is increased from R=8 to R=12 and the calf reference protocol parameters are used, then the view share factor can be decreased from N5 to N4 while maintaining a 2.5 sec image update time, allowing a reduced temporal footprint of 9.4 vs. 12.3 sec and an increased relative center diameter of 0.19 vs. 0.08. Alternatively, if the SENSE acceleration is kept at R=8 but the phase-encoded axial spatial resolution is allowed to increase from 1.0 to 1.5 mm 2, then the view share factor can be set to N3 with a 2.5 sec image update time, a 6.6 sec temporal footprint, and 0.15 relative center diameter. For either of these scenarios, the image update time and temporal footprint can be further reduced by decreasing the relative center diameter, which may be preferred for imaging stations with especially rapid contrast bolus propagation or limited sampling time.

In summary, time-resolved sampling strategies for real-time fluoroscopic tracking are provided that can address the limited imaging duration at proximal stations of a bolus chase MRA protocol. Rapid sampling of high spatial frequencies is used to improve image quality, and a short frame time is used for precise triggering of table motion. The present invention achieves these objectives by better trading off the spatial and temporal consequences of limited sampling.

The present invention has been described in terms of one or more preferred embodiments, and it should be appreciated that many equivalents, alternatives, variations, and modifications, aside from those expressly stated, are possible and within the scope of the invention.

The invention claimed is:

1. A method of producing a series of contrast-enhanced, time-resolved images of a vasculature of a subject over an extended field of view using a magnetic resonance imaging (MRI) system having a field of view that is less than the extended field of view, the method comprising the steps of:
   a) positioning the subject at an initial imaging station to image an initial portion of the vasculature of the subject with the MRI system;
   b) selecting imaging parameters;
   c) using the imaging parameters, performing a pulse sequence with the MRI system by:
      i) acquiring initial time-resolved image data from the initial portion of the vasculature of the subject using the MRI system;
      ii) during step i) reconstructing, in substantially real-time, a series of three-dimensional (3D) tracking images of the initial portion of the vasculature of the subject and identifying a current position of the contrast bolus provided to the subject as the contrast bolus passes through the initial portion of the vasculature;
      iii) based on the identified current position of the contrast bolus, moving the subject to a subsequent imaging station to image a subsequent portion of the vasculature of the subject with the MRI system;
      iv) acquiring subsequent time-resolved image data from the subsequent portion of the vasculature of the subject using the MRI system;
      v) during step iv) reconstructing, in substantially real-time, a series of 3D tracking images of the subsequent portion of the vasculature of the subject using the subsequent time-resolved image data and updating the identified current position of the contrast bolus provided to the subject as the contrast bolus passes through the subsequent portion of the vasculature;
      vi) repeating steps iii) through v) until image data has been acquired using the field of view of the MRI system from across the extended field of view; and
   d) assembling an image of the vasculature of the subject over the extended field of view using the initial time-resolved image data and the subsequent time-resolved image data.

2. The method of claim 1 wherein at least one of a spatial resolution and a temporal resolution of the subsequent time-resolved image data varies between repetition of steps iii) through v) at step vi).

3. The method of claim 1 wherein step iv) includes selecting at least one of a spatial resolution and a temporal resolution of the subsequent time-resolved image data based on the current position of the contrast bolus.

4. The method of claim 1 wherein the series of 3D tracking images of the intitial portion or the subsequent portion of the vasculature, or both, are fluoroscopic tracking images.

5. The method of claim 1 wherein at least one of the initial portion and the subsequent portion of the vasculature includes a peripheral vasculature of the subject.

6. The method of claim 1 wherein acquisition of time-resolved image data includes utilizing a SENSE acceleration technique.

7. The method of claim 1 wherein reconstruction includes utilizing a homodyne reconstruction technique.

8. The method of claim 1 wherein acquisition of time-resolved image data includes utilizing a view-sharing technique.

9. The method of claim 1 further comprising independently selecting between at least one of a SENSE acceleration technique, a homodyne reconstruction technique, and a view-sharing technique during performance of steps a) through c).

10. The method of claim 1, wherein selecting imaging parameters comprises selecting a combination of a SENSE acceleration technique, a homodyne reconstruction technique, and a view-sharing technique.

11. The method of claim 10 further comprises optimizing competing constraints of the combination of the SENSE acceleration technique, the homodyne reconstruction technique, and the view-sharing technique.

12. A magnetic resonance imaging (MRI) system having a field of view and configured to produce a series of contrast-enhanced, time-resolved images of a vasculature of a subject over an extended field of view that is greater than the field of view of the MRI system, the MRI system comprising:
   magnet system configured to generate a polarizing magnetic field about at least a portion of a subject arranged in the MRI system;
   a plurality of gradient coils configured to apply a gradient field to the polarizing magnetic field;

a radio frequency (RF) system configured to apply an excitation field to the subject and acquire MR image data therefrom;

a computer system programmed to at least carry out the steps of:
  a) positioning the subject at an initial imaging station to image an initial portion of the vasculature of the subject within the field of view of the MRI system;
  b) receiving imaging parameters;
  c) controlling the plurality of gradient coils and the RF system according to a pulse sequence configured using the imaging parameters to:
    i) acquiring initial time-resolved image data from the initial portion of the vasculature of the subject using the MRI system;
    ii) during step i), reconstructing, in substantially real-time, a series of three-dimensional (3D) tracking images of the initial portion of the vasculature of the subject and identifying a current position of the contrast bolus provided to the subject as the contrast bolus passes through the initial portion of the vasculature;
    iii) based on the identified current position of the contrast bolus, moving the subject to a subsequent imaging station to image a subsequent portion of the vasculature of the subject within the field of view of MRI system;
    iv) acquiring subsequent time-resolved image data from the subsequent portion of the vasculature of the subject using the MRI system;
  d) during step c)iv) reconstructing, in substantially real-time, a series of 3D tracking images of the subsequent portion of the vasculature of the subject using the subsequent time-resolved image data and updating the identified current position of the contrast bolus provided to the subject as the contrast bolus passes through the subsequent portion of the vasculature;
  e) repeating steps c)iii) through d) until image data has been acquired using the field of view of the MRI system from across the extended field of view; and
  f) assembling an image of the vasculature of the subject over the extended field of view using the initial time-resolved image data and the subsequent time-resolved image data.

13. The system of claim 12 wherein the computer system is further programmed to vary at least one of a spatial resolution and a temporal resolution of the subsequent time-resolved image data between repetition of steps c)iii) through d) at step e).

14. The system of claim 12 wherein the computer is further programmed to select at least one of a spatial resolution and a temporal resolution of the subsequent time-resolved image data based on the current position of the contrast bolus for each repetition of step d)iv).

15. The system of claim 12 wherein the series of 3D tracking images of the initial portion or the subsequent portion of the vasculature, or both, are fluoroscopic tracking images.

16. The system of claim 12 wherein at least one of the initial portion and the subsequent portion of the vasculature includes a peripheral vasculature of the subject.

17. The system of claim 12 wherein the computer is further programmed to independently select between at least one of a SENSE acceleration technique, a homodyne reconstruction technique, and a view-sharing technique during performance of steps a) through e).

18. The system of claim 12, wherein the computer system is further programmed to determine competing constraints of a combination of a SENSE acceleration technique, a homodyne reconstruction technique, and a view-sharing technique.

19. The system of claim 18, wherein the computer system is further programmed to select imaging parameters that optimize the competing constraints of the combination of the SENSE acceleration technique, the homodyne reconstruction technique, and the view-sharing technique.

* * * * *

UNITED STATES PATENT AND TRADEMARK OFFICE
CERTIFICATE OF CORRECTION

PATENT NO. : 9,700,229 B2  
APPLICATION NO. : 13/435547  
DATED : July 11, 2017  
INVENTOR(S) : Stephen J Riederer et al.

Page 1 of 1

It is certified that error appears in the above-identified patent and that said Letters Patent is hereby corrected as shown below:

Column 15, Line 9, "NP" should be --A/P--.

Column 18, Line 16, "NP" should be --A/P--.

Column 18, Line 18, "NP" should be --A/P--.

Column 20, Claim 12, Line 63, "magnet system" should be --a magnet system--.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*